(12) United States Patent  
Blok (10) Patent No.: US 7,138,090 B2
(45) Date of Patent: Nov. 21, 2006

(54) VAPOR SENSOR AND MATERIALS THEREFOR

(75) Inventor: Edward J Blok, Wadsworth, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 66 days.

(21) Appl. No.: 10/411,805

(22) Filed: Apr. 11, 2003

(65) Prior Publication Data

US 2004/0202856 A1   Oct. 14, 2004

(51) Int. Cl.
*G01N 31/00* (2006.01)

(52) U.S. Cl. ............... 422/82.01; 422/50; 422/55; 422/56; 422/68.1; 422/82.02; 422/82.03; 436/149

(58) Field of Classification Search .......... 422/50, 422/55, 56, 57, 68.1, 86, 88, 90, 82.01, 82.02, 422/83; 436/166, 149
See application file for complete search history.

(56) References Cited

U.S. PATENT DOCUMENTS

| | | | |
|---|---|---|---|
| 3,045,198 A | 7/1962 | Dolan et al. | |
| 3,848,218 A | 11/1974 | Wakabayashi et al. | |
| 3,864,659 A | 2/1975 | Furuuchi et al. | |
| 4,129,030 A | 12/1978 | Dolan | |
| 4,224,595 A | 9/1980 | Dolan | |
| 4,592,967 A | 6/1986 | Komatsu et al. | |
| 4,621,249 A | 11/1986 | Uchikawa et al. | |
| 4,631,952 A | 12/1986 | Donaghey | |
| 4,673,910 A | 6/1987 | Uchikawa et al. | |
| 4,686,524 A | 8/1987 | White | |
| 4,691,186 A | 9/1987 | Shin et al. | |
| 4,752,761 A | 6/1988 | Dolan et al. | |
| 4,938,860 A * | 7/1990 | Wogoman | 204/403.05 |
| 5,150,603 A | 9/1992 | Boenning et al. | |
| 5,256,574 A | 10/1993 | Neuburger et al. | |
| 5,283,308 A | 2/1994 | Bilgrien et al. | |
| 5,571,401 A | 11/1996 | Lewis et al. | |

(Continued)

FOREIGN PATENT DOCUMENTS

EP       0 434 396 B1       11/1994

(Continued)

OTHER PUBLICATIONS

Grate, Jay, "Solubility Properties of Siloxane Polymers for Chemical Sensors", Proceedings of SPIE-The International Society for Optical Engineering, 2574 (1995), 71-7.

(Continued)

*Primary Examiner*—Jill Warden
*Assistant Examiner*—Sam P. Siefke
(74) *Attorney, Agent, or Firm*—Harness, Dickey & Pierce, PLLC (57) ABSTRACT

The present invention relates to a composition for sensor films used for detecting chemical analytes within sensors, such as polymer-absorption chemiresistors (i.e. conductometric sensors). The present invention provides sensor film compositions that have greater temperature stability and sensitivity to chemical analytes, as well as methods of making these sensor films. Sensor film compositions according to the present invention include a crosslinked siloxane polymer comprising a monomer having a hydrocarbon side group with greater than or equal to two carbon atoms and a plurality of conductive particles distributed within the polymer. Alternate preferred embodiments distribute an oil comprising siloxane having at least one side group with greater than or equal to two carbons through a crosslinked siloxane polymer, wherein the oil is distributed through a crosslinked polysiloxane copolymer. Further, conductive particles having a $N_2$ adsorption of between about 8 to about 25 $m^2/g$ provide enhanced sensor film performance.

22 Claims, 3 Drawing Sheets

U.S. PATENT DOCUMENTS

| | | | |
|---|---|---|---|
| 5,610,324 | A | 3/1997 | Lawson |
| 5,788,833 | A | 8/1998 | Lewis et al. |
| 5,891,398 | A | 4/1999 | Lewis et al. |
| 5,911,872 | A | 6/1999 | Lewis et al. |
| 5,951,846 | A | 9/1999 | Lewis et al. |
| 5,959,191 | A | 9/1999 | Lewis et al. |
| 5,979,227 | A | 11/1999 | Lawson et al. |
| 6,013,201 | A | 1/2000 | Hayashida et al. |
| 6,042,788 | A | 3/2000 | De Wit et al. |
| 6,170,318 | B1 | 1/2001 | Lewis |
| 6,217,828 | B1* | 4/2001 | Bretscher et al. ........ 422/82.07 |
| 6,342,295 | B1 | 1/2002 | Kobayashi |
| 6,433,694 | B1 | 8/2002 | Dolan et al. |
| 6,444,323 | B1 | 9/2002 | Matsumoto et al. |
| 6,455,319 | B1 | 9/2002 | Lewis et al. |
| 6,868,350 | B1* | 3/2005 | Zimmermann et al. ....... 702/65 |

FOREIGN PATENT DOCUMENTS

| | | |
|---|---|---|
| EP | 0 833 421 A2 | 4/1998 |
| EP | 1 088 849 A2 | 4/2001 |
| JP | 02-309090 | 12/1990 |
| JP | 05-043823 | 2/1993 |
| JP | 07-258548 | 2/1993 |
| JP | 08-020725 | 1/1996 |
| JP | 08-120176 | 5/1996 |
| JP | 11-106657 | 4/1999 |
| JP | 2001-158856 | 6/2001 |
| JP | 2001-221225 | 8/2001 |
| RU | 1 582 597 A1 | 11/1995 |
| WO | WO 96/37547 | 11/1996 |
| WO | WO 99/53300 | 10/1999 |
| WO | WO 01/88042 A1 | 11/2001 |
| WO | WO 02/08314 | 1/2002 |
| WO | WO 02/23134 A1 | 3/2002 |

OTHER PUBLICATIONS

Ho et al., "Review of Chemical Sensors for in-Situ Monitoring of Volatile Contaminants", SAND2001-0643, Mar. 2001.

Ronot et al., "Detection of chemical vapours with a specifically coated optical-fibre sensor," Sensors and Actuators B, 11 (1993) 375-381.

Ronot et al., "Optimization and performance of a specifically coated intrinsic optical-fibre sensor for the detection of alkane compounds," Sensors and Actuators A, 41-42 (1994) 529-534.

Ronot-Trioli et al., "Solubility Interactions between Organic Vapors and Specific Polymeric Claddings for Optical Fiber Sensor," Sensors and Materials, vol. 7, No. 6, (1995) 383-393.

Schierbaum, "Application of organic supramolecular and polymeric compounds for chemical sensors," Sensors and Actuators B, 18-19 (1994), 71-76.

European Search Report for EP 04076097; Dated Jul. 30, 2004.

* cited by examiner

VAPOR SENSOR AND MATERIALS THEREFOR

FIELD OF THE INVENTION

The present invention relates to sensor films, and more particularly to sensor films that detect vapor analytes.

BACKGROUND OF THE INVENTION

Detection of specific target analytes, or chemical compounds, is important for many applications, including for example, detecting whether the concentration of analytes exceeds flammability limits. Target analytes are detected by sensors operating according to different detection mechanisms, known in the art. Most sensors employ a sensing component that is physically modified in the presence of specific analytes present in the environment. Thus, a sensor typically comprises a probe that includes both the sensing component and a probe body housing (including terminals for transmitting an output). The terminals are typically coupled to a processor, also part of the sensor, which analyzes the outputs received from the sensor probe to a user interface. Such a user interface typically contains an indicating device which signals a user when concentration values of an analyte have been exceeded.

Many sensors employ a sensing component that is a sensor film. Many sensor films swell, increasing in volume, while in the presence of the analytes. Various sensors available in the art utilize the physical changes in the sensor film to determine concentration of analyte present. Such sensors may include optical sensors, such as fiber optic sensors, where a beam of light is projected through an optical fiber at a sensor film cladding, and physical changes (e.g. refractive index or color) in the film are monitored. Such changes in refractive index occur when analytes are absorbed and change the physical properties of the cladding (including volumetric changes). Other sensors include sound acoustic wave sensors (SAWS), which project ultrasonic waves through the sensor film between transducers, and likewise detect any modifications in the properties of the sensor film (primarily the mass), translating those changes to the concentration of analyte present.

Another type of sensor film is a conductometric sensor, more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. The polymer absorbs target analytes and this results in a volumetric change of the film, and hence the electrical resistance of the film. Further, conductive particles may be distributed throughout the polymer film to enhance the sensitivity to resistance changes in the material when the volume of the polymer changes. However, any sensor film that relies upon physical changes resulting from absorption of the chemical analytes (i.e. volume, mass, refractive index, and resistance) is generally also sensitive to volumetric changes dependent on temperature. Further, enhancing the sensitivity to chemical analytes is desirable. There is a need for a sensor film composition that enhances sensitivity to desired chemical analytes, while further increasing its stability during temperature fluctuations.

SUMMARY OF THE INVENTION

The present invention provides a sensor film for detecting chemical analytes. In one preferred embodiment, a conductometric sensor film comprises a crosslinked siloxane polymer comprising a monomer having a hydrocarbon side group with greater than or equal to two carbon atoms; and a plurality of conductive carbon black particles having a $N_2$ adsorption of between about 8 to about 25 $m^2/g$, distributed within the polymer.

Alternate preferred embodiments of the present invention include a sensor film composition for detecting chemical analytes comprising a crosslinked polymer that comprises a siloxane monomer having a hydrocarbon side group with greater than or equal to two carbon atoms, and a plurality of conductive particles distributed in the crosslinked polymer.

In another preferred embodiment of the present invention, a sensor film composition for detecting chemical analytes comprises a polymer comprising siloxane; and a plurality of conductive particles having a $N_2$ adsorption of between about 8 to about 25 $m^2/g$; wherein the conductive particles are distributed in the polymer.

In another alternate preferred embodiment, a sensor film composition for detecting chemical analytes comprises a crosslinked polymer comprising siloxane, and an oil comprising a hydrocarbon side group substituted siloxane. The hydrocarbon side group comprises greater than or equal to two carbon atoms, wherein the oil is distributed through the crosslinked polymer.

Alternate preferred embodiments of the present invention include a method of making a sensor film and comprise the steps of admixing a polymer comprising a siloxane monomer having a hydrocarbon side group with greater than or equal to two carbon atoms, and at least one monomer having a functional group, a plurality of conductive particles, a curing reagent; and a catalyst. Then the polymer, conductive particles, curing reagent, and catalyst are mixed to form a matrix mixture, which is applied on a sensor probe. The matrix mixture is crosslinked.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

The present invention contemplates a sensor film having improved temperature stability and sensitivity to analytes. One aspect of the present invention includes the addition of alkyl branched siloxane oil to a siloxane based sensor film. Another aspect of the present invention incorporates an alkyl substituent side group into a crosslinked siloxane polymer sensor film. A further aspect of the present invention incorporates conductive carbon black particles having large particle sizes for improved sensor operation.

Figure 1:
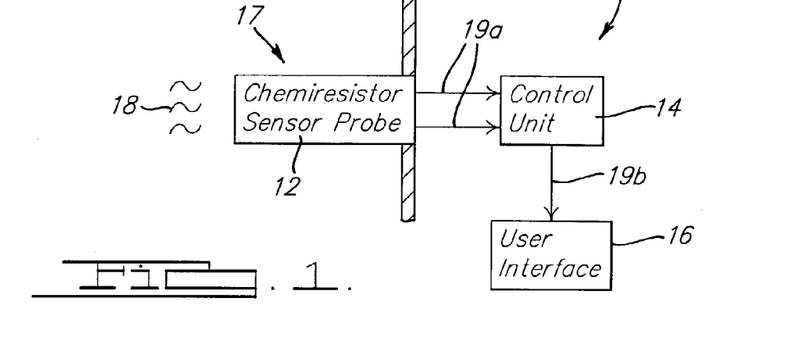
FIG. 1 is a schematic illustration of operational principles of an exemplary chemiresistor sensor.

FIG. 1 generally depicts the major components and operational principles of an exemplary chemiresistor sensor at 10. The sensor 10 is generally comprised of a chemiresistor sensor probe 12, a control unit 14, and a user interface 16. The sensor probe 12 interacts with an external environment 17 to detect the presence of analytes, or target chemical compositions 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19 a from the sensor probe 12. The user interface 16 provides information to an external user about the sensor 10 and may range from a simple alarm signal to a complex computerized screen.

Figures 2, 3:
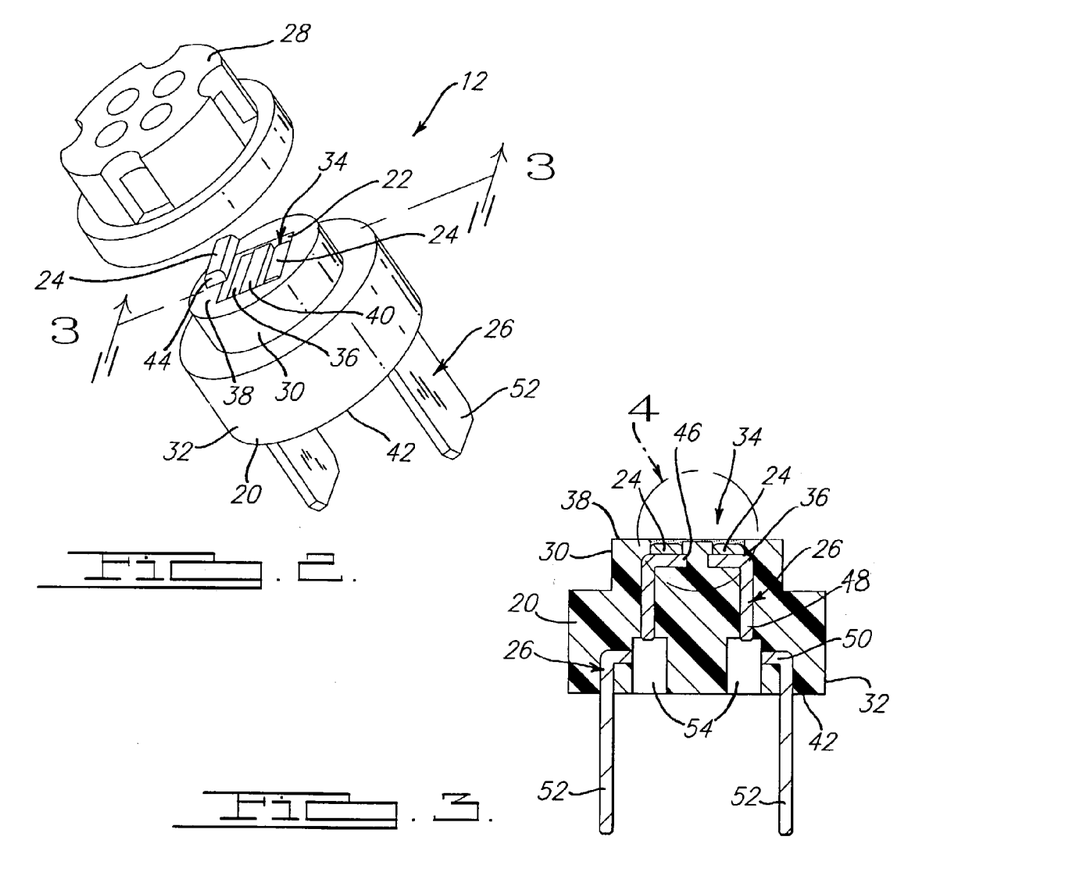
FIG. 2 is a schematic illustration of an exemplary chemiresistor sensor that can be used in accordance with the present invention.
FIG. 3 is a cross-sectional view taken along line 3—3 of FIG. 2.

Referring generally to FIG. 2, an example of a polymer-absorption chemiresistor sensor probe 12 compatible with the sensor film compositions of the teachings of the present invention is shown. The sensor probe 12 generally comprises a sensor housing 20, a conductive sensor film 22 covering a portion of the sensor housing 20 (FIGS. 2 and 3), a pair of electrodes 24 optionally disposed beneath and attached to the sensor terminals 26, and a protective cap 28. In lieu of electrodes, an alternate sensor embodiment is feasible, where the terminals 26 protrude into the sensor film 22, and serve a similar function to the electrodes 24 (i.e. deliver current through the sensor film 22).

The sensor housing 20 includes a first diameter portion 30 and a second diameter portion 32, wherein the first diameter portion is smaller in diameter than the second diameter portion. The first diameter portion 30 includes a sensing region 34. The sensing region 34 is comprised of two apertures 36 located within a first control surface 38 of the sensing region 34. Between the apertures 36 is a recessed second control surface 40 that extends across the sensing region 34. The second control surface 40 is slightly recessed below the first control surface 38.

Figure 4:
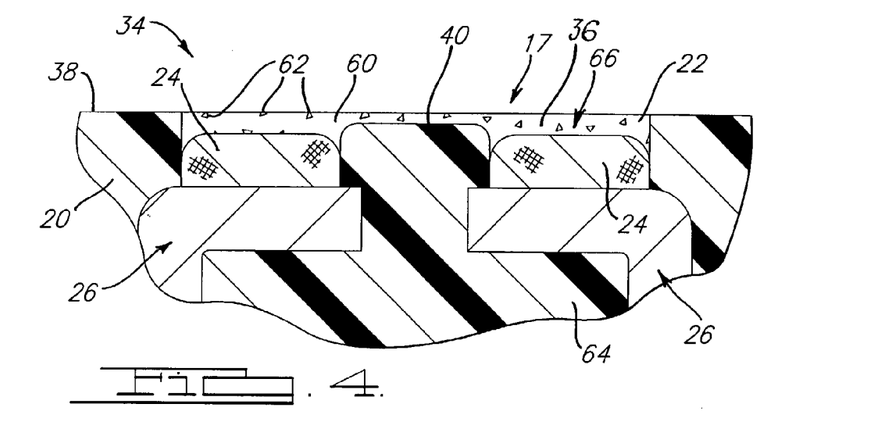
FIG. 4 is a detailed view of an exemplary sensor film region.

As best shown in FIG. 3, a cross-sectional view along line 3–3 of FIG. 2, each electrode 24 sits above the apertures 36. Terminals 26 are attached to the electrodes 24 and extend through both the first diameter portion 30 and the second diameter portion 32. The terminals 26 protrude from the housing 20 at an underside 42 of the second diameter portion 32. The electrodes 24 and terminals 26 are made of a conductive material, preferably a metal. With specific reference to FIG. 4, the electrodes 24 each comprise a horizontal porous plate or mesh that is parallel to the first control surface 38 and approximately equals the width of the aperture 36. Each electrode 24 is connected to establish a conductive pathway to terminal 26. With renewed reference to FIGS. 2 and 3, a first horizontal portion 46 of the terminal 26 makes either direct or indirect contact with the portion of the sensor film 22 seated within the apertures 36 to detect changes in the resistance of the sensor film 22. Extending from the first horizontal portion 46 is a first vertical portion 48. The first vertical portion 48 extends through the first diameter portion 30 and into the second diameter portion 32 where the first vertical portion 48 transitions to an inner terminal dogleg 50 that ends in the external terminals 52 (i.e. end leads).

At the transition point between the first vertical portion 48 to the inner terminal dogleg 50, the terminals 26 each have an aperture 54. The aperture 54 receives an alignment rod (not shown) during manufacturing to permit more precise alignment of the electrodes 24 within the housing 20. The inner terminal dogleg 50 extends to the external terminals 52 which extend from the underside 42 of the second diameter portion 32. The external terminals 52 extend from the housing 20 to a suitable length to permit interconnecting the leads to a corresponding outlet (not shown) of a suitable alert device, such as an alarm.

As best seen in FIG. 3, a detailed view of the sensing region 34 from FIGS. 1 and 2, the sensor film 22 comprises a polymer 60 with conductive particles 62 dispersed throughout. The terminals 26 extend through a body 64 of the sensor probe housing 20 and are electrically connected to the electrodes 24. The electrodes 24 protrude into the sensing region 34 and into the sensor film 22. The electrodes 24 preferably are situated near the surface, and further across the sensor film, for even current distribution. A preferable configuration of the sensor film 22 includes conductive particles 62 distributed homogeneously (i.e. evenly) throughout the sensor film 22 body forming a conductive polymeric matrix 66. "Matrix" refers generally to a polymer system having filler particles distributed throughout within the polymer.

The conductive sensor film matrix 66 is seated upon the first control surface 38 such that the matrix 66 fills the apertures 36 and spans the center second control surface 40. The matrix 66 fills the apertures 36 so that the matrix 66 is in either direct or indirect electrical contact with both of the electrodes 24. Upon exposure of the matrix 66 to target analytes, the matrix 66 volume increases by swelling.

The polymer 60 of the sensor film 22 can be any polymer that readily absorbs a target analyte or chemical compound, through a gas-solid interface occurring between a surface of the sensor film 22 and the surrounding gas in the external environment 17 (FIG. 1) at a rate that is relatively proportional to the concentration of the analyte in the surrounding gas. Thus, a correlation can be made between the quantity of analyte absorbed, and the concentration of the analyte in the surrounding gas. In the exemplary sensor probe 12 depicted, the change in the volume of the sensor film 22 is correlated to the concentration of the analyte present in the gas and is further related to the resistance of the sensor film 22. Of particular interest are sensor films 22 that detect vaporous hydrocarbon compounds, such a volatile organic compounds (VOCs). Compatible polymers for detecting VOCs include siloxane polymers. A variety of siloxane based polymers are contemplated in the present and invention, and further discussed below.

Figure 5:
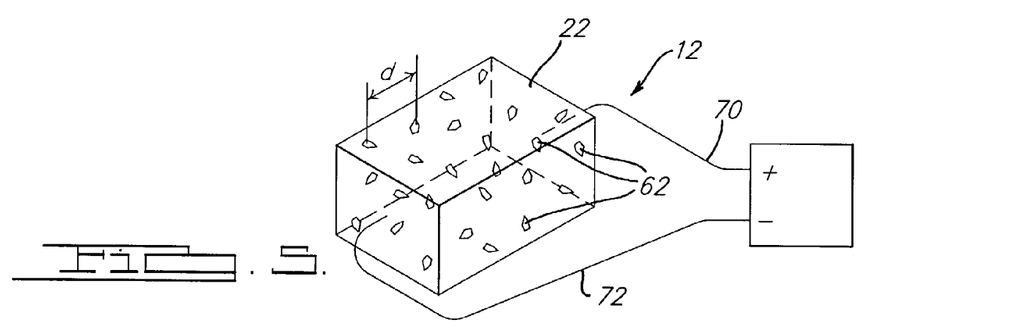
FIG. 5 is a schematic illustration of operating principles of a matrix polymer film of a polymer absorption chemiresistor.

As shown in FIG. 5, the operational principle of a polymer-absorption chemiresistor sensor probe 12 involves applying a current through the sensor film 22 between a positive 70 and a negative lead 72. Preferably, the positive and negative leads 70, 72 are electrodes, such as those shown at 24 in FIGS. 2 and 3. Conductive particles 62 are distributed throughout the sensor film 22 to enhance the electrical conductivity. Resistance measurements are taken across the sensor film 22 via monitoring of the current and potential difference across the sensor film 22 between the negative and positive leads 70, 72, and typically is measured by the processing or control unit 14 (FIG. 1) attached to the sensor probe 12. Resistance values vary with the distance "d" between the conductive particles. As this distance "d" between the conductive particles 62 increases, the resistance has a proportional relationship and thus increases. If the distance "d" decreases, the resistance also decreases. Thus, any increase or decrease in the volume of the sensor film 22 affects the overall resistance measurements. Upon detection of a change in resistance between the positive and negative leads 70, 72, the user interface 16 (FIG. 1) provides a signal indicating the presence of the substance for which the sensor film 22 has an affinity. Consequently, the change in resistance of the sensor film 22 detected by the electrodes 70, 72 indicates the presence of the target analyte. The sensor film 22 volume may increase both by changes in temperature, as well as absorption of chemical compounds, or target analytes, into the polymer of the sensor film 22. One aspect of the present invention relates to minimizing effects of volume changes of the sensor film 22 due to temperature, and maximizing the absorption and sensor film 22 sensitivity to chemical compounds.

A "siloxane polymer" as used herein, refers to a cross-linked polymer that has a basic backbone of silicon and oxygen with side constituent groups that may be the same or different, generally described by the structural repeating unit (—O—SiRR'—)$_n$, where R and R' may be the same or different side constituent groups, and n may be any value above 2 designating the repetition of the SRU in the polymer backbone. Siloxane polymers are also known in the art as "silicone" polymers. Siloxane polymers may include polyheterosiloxanes, where side groups and/or structural repeating units may be different entities (having different side constituent groups), such as, for example, the siloxane co-polymer described by the nominal SRU formula, (—O—SiRR')$_n$—(—O—Si—R"R'")$_m$, wherein R and R' are distinct side groups from R" and R'". Further R and R' may be different from one another, likewise the same may be true for R" and R'". Such siloxane polymers may terminate in any variety of terminal groups, such as for example, trimethyl silyl ((CH$_3$)$_3$Si) terminated siloxane, or ethyl vinyl terminated siloxane.

In one preferred embodiment of the present invention, the polymer of the sensor film is a cross-linked dimethylsiloxane (—O—SiRR')$_n$, where R and R' are both CH$_3$. A siloxane oil is added to the polymer base of the sensor film. "Siloxane oil", as used herein, refers generally to siloxane based compounds that are polymerized to form siloxane polymer compounds, but are not subjected to or capable of subsequent crosslinking, and therefore are not crosslinked. Preferably, the siloxane oil polymeric compounds have a relatively low molecular weight, which correlates to a lower viscosity siloxane oil which is generally preferable for the present invention. When added to the siloxane polymer, the siloxane oil is suspended in the polymer and has freedom of movement to diffuse based on concentration gradients throughout the polymer film. Preferred siloxane oils for the present invention include those with substituted side groups comprising hydrocarbons or side groups derived from hydrocarbons, comprising at least two carbon atoms, such as for example, alkyl, aryl, and aromatic side groups, and may comprise copolymers. Such side groups may be referred to as "branched" indicating side groups attached to the siloxane backbone. Particularly preferred are alkyl branched, or substituted, siloxanes with alkyl groups having ethyl (i.e. two carbon atoms) groups or greater. Non-limiting examples of such alkyl hydrocarbon side groups include: ethyl, propyl, butyl, pentyl, hexyl, heptyl, octyl, nonyl, decyl, tetradecyl, octadecyl. Other preferred hydrocarbon-derived side groups, include for example, N-pyrrolidonepropyl, cyanopropyl, benzyltrimethyl ammonium chloride and hydroxyalkyl functional groups. Some examples of preferred siloxane oils according to the present invention include: polyloctylmethylsiloxane, polytetradecylmethylsiloxane, polyoctadecylmethylsiloxane and hexylmethylsiloxane—PhenylpropylMethylsiloxane copolymer.

The amount of siloxane oil added to the polymer in the sensor film of the present invention is preferably between about 1 to about 40 weight percent of the total polymer film weight, with the most preferred amount being about 15 to about 20 weight percent. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates a possible variation of up to 5% in the value. The siloxane oil may be charged or added to the siloxane polymer before or after the conductive particles 62 are added prior to being formed into the sensor film body 22.

Figure 6:
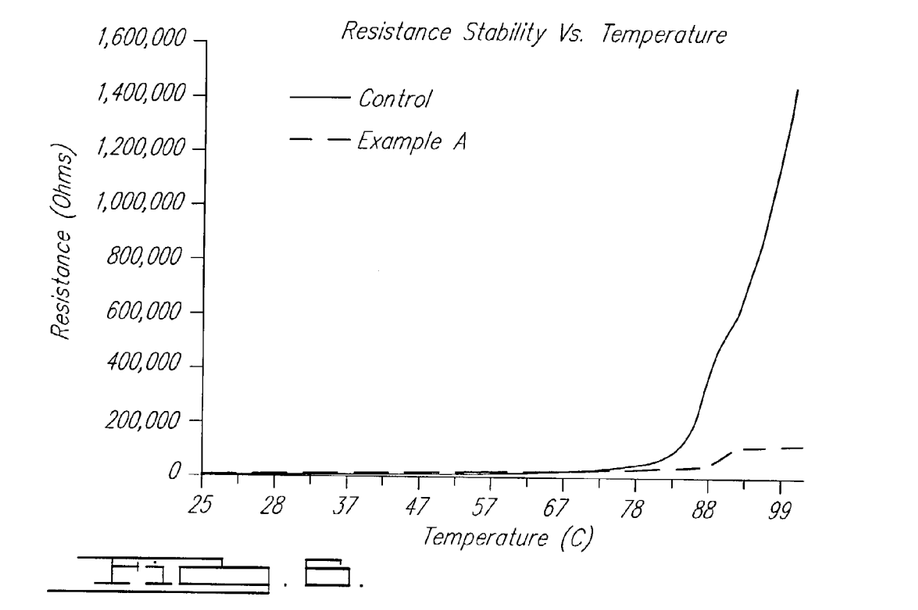
FIG. 6 is a chart of resistance stability versus temperature comparing a prior art dimethylsiloxane film with a preferred embodiment of the present invention.

Referring to FIG. 6, comparative data is provided showing the resistance stability of a prior art sensor film, designated as "control" which is made of 100 parts by weight of dimethyl silicone and 75 parts by weight of a conductive carbon black particle (standard rubber black N762). A sensor made according to the embodiment disclosed above, having siloxane oil added is identified as Example A. Example A was prepared with 85 parts by weight dimethyl silicone; 15 parts by weight polyoctylmethyl silicone oil, and 75 parts by weight of N762 carbon black particles. Tests were conducted with the Control and Example A (incorporated into sensor probes) where the sensor probes were positioned 14.3 cm above 50 ml of 2-methylbutane solvent in an 8.5 liter container. Measurements of resistance (Ohms) were taken over a range of temperatures from approximately 26 to 100° C. As can be observed, Example A exhibited greater stability over the entire temperature range, as where the control showed far less stability at temperatures above 80° C. where resistance spiked.

Additional comparative data for the Control and Example A is shown in Table 1 below, demonstrating relative response times to reach various resistance levels. The response times were recorded with respect to resistance during the testing described above (results from three samples were averaged). The relative response times to reach the percentage change of resistance levels for both the Control and Example A are very similar to one another. Thus, the fundamental trade-off between temperature sensitivity (swelling) and sensitivity to analytes has been improved. The Control changes 200% in resistance at 61.2° C. while Example A reaches a 200% change in resistance at 73.6° C. In the present embodiment of the present invention, a sensor film has reduced sensitivity to temperature, and further has comparable response times to the prior art, resulting in an overall enhancement of sensor performance.

TABLE 1

| Time to reach % change in Resistance | 50% | 100% | 150% | 200% |
|---|---|---|---|---|
| Control - average of 3 samples (Seconds) | 570 | 980 | 1290 | 1550 |
| Example A - average of 3 samples (Seconds) | 580 | 1010 | 1290 | 1550 |

In an alternate preferred embodiment of the present invention, the sensor film 22 comprises a crosslinked siloxane polymer base, wherein the siloxane polymer backbone has at least one monomer with a large hydrocarbon substituted side group represented by R' in the nominal general formula for the structural repeating unit $(-O-SiRR')_n$. A "hydrocarbon side group", as used herein, includes any hydrocarbon or hydrocarbon derived side group with two carbon atoms or greater. Examples of such hydrocarbon side groups include: alkyl and aryl groups greater than ethyl, branched alkyl groups, aromatics, modified hydrocarbon compounds comprising a polar groups, or mixtures thereof. Polar group modified hydrocarbons incorporate a polar molecule or molecular group into the hydrocarbon side group structure, with the effect of imparting polarity on the entire side group. Such polar atoms or groups may include, for example, oxygen, nitrogen, or ammonia, cyano or hydroxyl groups. Examples of preferred hydrocarbon side groups include without limitation: ethyl, propyl, butyl, pentyl, hexyl, heptyl, octyl, nonyl, decyl, phenyl, alkylphenyl, cyclopentyl, and phenylpropyl. Other preferred hydrocarbon side groups comprising a polar group include, for example, butylated aryloxypropyl, N-pyrrolidonepropyl, cyanopropyl, benzyltrimethyl ammonium chloride and hydroxyalkyl.

One example of such a siloxane having a large hydrocarbon side group includes an octyl hydrocarbon side group that forms an octylmethylsiloxane monomer. It is preferable that the siloxane polymer according to the present embodiment is crosslinked, and thus also contains a functional group capable of crosslinking during any subsequent curing or crosslinking processes. Preferred crosslinked siloxane polymers include those polymers (including homopolymers and copolymers) having at least one large hydrocarbon side substituent group. As used herein, the term "polymer" encompasses homopolymers and copolymers. The term "copolymer" generically refers to a polymeric structure that has two or more monomers polymerized with one another, and includes polymers such as terpolymers with three combined monomers. A "homopolymer" refers to a polymer comprised of a single monomer. One example of a preferred crosslinked siloxane having a copolymer (e.g. terpolymer) structure is poly(vinylmethylsiloxane-octylmethylsiloxane-dimethylsiloxane). Thus, the terpolymer structure has vinyl functional groups that are capable of crosslinking when exposed to crosslinking or curing agents. Ranges of the quantity of monomers in the terpolymer include (3–5% vinylmethylsiloxane)-(35–75% octylmethysiloxane)-(20%–62% dimethylsiloxane), wherein the octyl is the hydrocarbon side group, R', incorporated into the siloxane monomer, and R is a methyl side group. Another example of a preferred crosslinked siloxane having a large hydrocarbon side group according to the present invention is a polyphenylmethylsiloxane, where the phenyl is the large hydrocarbon side group and the polymer has vinyl terminal groups for subsequent crosslinking.

Incorporation of large hydrocarbon side groups into monomers (which are further incorporated into polymers according to the present invention) is achieved by polymerization performed in a conventional manner. Such a monomer, having a side group, is preferably functionalized by incorporating a reactive functional group (e.g. epoxy, amine, mercapto, methacrylate/acrylate, acetoxy, chlorine; hydride or vinyl; or hydroxyl groups) to facilitate incorporation into the siloxane backbone by polymerization, such as by conventional methods known in the art. In the case of poly(vinylmethylsiloxane-octylmethylsiloxane-dimethylsiloxane), discussed above, the octylmethylsiloxane monomer is incorporated into a copolymer with other monomers of dimethylsiloxane and vinylmethyl siloxane, where the octylmethylsiloxane monomer is preferably present in the range of from about 35% to about 75%. The octylmethylsiloxane monomer displaces the dimethylsiloxane monomer. In the case of polyphenylmethylsiloxane, substantially all of the polymer chain comprises the phenylmethylsiloxane monomer, except for the terminal ends of the siloxane polymer which are vinyl terminated (e.g. dimethylvinyl terminated siloxane). Such monomer ranges are exemplary and non-limiting and are dependent upon specific characteristics of the individual monomers employed. It is preferable to maximize the quantity of large hydrocarbon side group substituted monomers in the siloxane polymer, because maximizing the amount of large hydrocarbon side groups in a siloxane based polymer sensor film has been shown to increase the overall temperature stability and analyte sensitivity.

After the large hydrocarbon side group siloxane base copolymer is formed (by a conventional polymerization reaction), the polymer further undergoes cross-linking after incorporation into the sensor film. Such crosslinking may be carried out by conventional means, such as by exposure to irradiation or peroxide, moisture cure by a condensation reaction, or a hydrosilylation reaction in the presence of a catalyst. Any method of crosslinking siloxane polymers may be used with the present invention, as recognized by one of skill in the art. A preferred method of crosslinking is the hydrosilylation reaction in the presence of a catalyst, which can generally be conducted at lower temperatures and where the control over the degree of crosslinking is greater.

Crosslinking by hydrosilylation generally requires a catalyst and a crosslinking (curing) reagent which reacts with accessible functional groups on at least some of the side groups within the siloxane polymer. One example of a hydrosilylation crosslinking reaction includes, for example, polyethylhydrosiloxane as a crosslinking reagent in the presence of a platinum catalyst to result in a crosslinked siloxane polymer. Polyethylhydrosiloxane is commercially available as the product HES-992, from Gelest, Inc. of Tullytown, Pa. The hydrosilylation reaction facilitates crosslinking between neighboring siloxane chains at the functional group sites. Other feasible catalyst systems that may be used for hydrosilylation (in addition to platinum) in the present invention include, for example: platinum carbonyl cyclovinylmethyliloxane complex used for elevated cures, such as SIP 6829 which is also commercially available from Gelest, Inc.; Rh(I) catalysts such as $(PPh_3)_3RhCl$ or $[(C_2H_4)_2RhCl]_2$, Ni catalysts, $(PPh_3)PdCl_2$, $Rh_2(OAc)_4$, $Ru_3(CO)_{12}$, and $Co_2(CO)_8$ and equivalents thereof. Functional groups must be present along the siloxane backbone or at the chain ends to allow for subsequent crosslinking after polymerization. The distinct monomers within any of the copolymers may be distributed randomly or may be regularly ordered.

Another preferred alternate embodiment of the present invention further enhances sensor operations and includes a sensor film matrix 22 incorporating conductive particles 62 with relatively low surface area values and DBP absorption values, in essence, conductive particles that are larger in particle size and lower in aggregate size, than prior art conductive particles. Distribution of the conductive particles 62 throughout the polymer base 60 can be achieved by mixing the conductive particles 62 into a polymer mixture prior to application on the sensor probe 12 to form a matrix mixture which forms the polymer base 60 of the sensor film 22. Preferably, the conductive particles 62 are homogeneously distributed throughout the polymer matrix base 60, to enhance the uniformity of resistance measurements.

Carbon black particles may be characterized by particle size, surface area per weight, and structure. A correlation generally exists between surface area and particle size, where a smaller particle diameter gives rise to a higher surface area. Likewise, a lower surface area value generally indicates a larger particle size diameter. Surface area is generally tested by the level of nitrogen adsorption ($N_2$) values in $m^2/g$. Testing procedures for nitrogen adsorption are outlined for example, in ASTM test D3037-91. Conductive carbon black particles in accordance with the present invention preferably have a $N_2$ adsorption value (surface area per weight) of between about 8 to about 25 $m^2/g$. The most preferred ranges of $N_2$ adsorption for the preferred embodiment of the present invention are between about 10 to about 15 $m^2/g$.

Further, the conductive carbon black particles are characterized by structure, or the configuration, of individual particles forming an aggregate. Structure can be tested by oil dibutylphthalate (DBP) absorption in accordance with test procedure ASTM D2414, where DBP is added to 100 grams of carbon black while being mixed to generate a value of DBP ml/100 grams. A sharp increase in the torque determines the DBP value. This test indicates the structure of the particles by measuring the size of the particle aggregate. The ranges of DBP for conductive carbon black particles according to the present invention preferably range from about 1 to about 180 ml/100 g.

A variety of conductive particles 62 may be used with the present invention, as recognized by one of skill in the art, such as, for example, gold, platinum, graphite (i.e., hexagonally crystallized carbon), carbon black, nickel, silver, conductive metal borides, nitrides or carbides. Most preferably, the conductive particles will comprise carbon black. Examples of commercially available conductive carbon black particles that fulfill the preferred physical characteristic ranges above include: Asahi 15HS or AS N880, both manufactured by Asahi Carbon Co., Ltd. of Japan; or CC N880 from Cancarb Ltd. of Alberta, Canada; and Spheron® 5000 or Spheron® 6000 both available from the Cabot Corporation of Boston, Mass. Preferred ranges of the mean particle size are from about 90 to about 400 nanometers. The amount of conductive particles added is dependent on the individual characteristics of the particle selected, but can range from about 25 to about 75 percent by weight of the total mixture.

Figure 7:
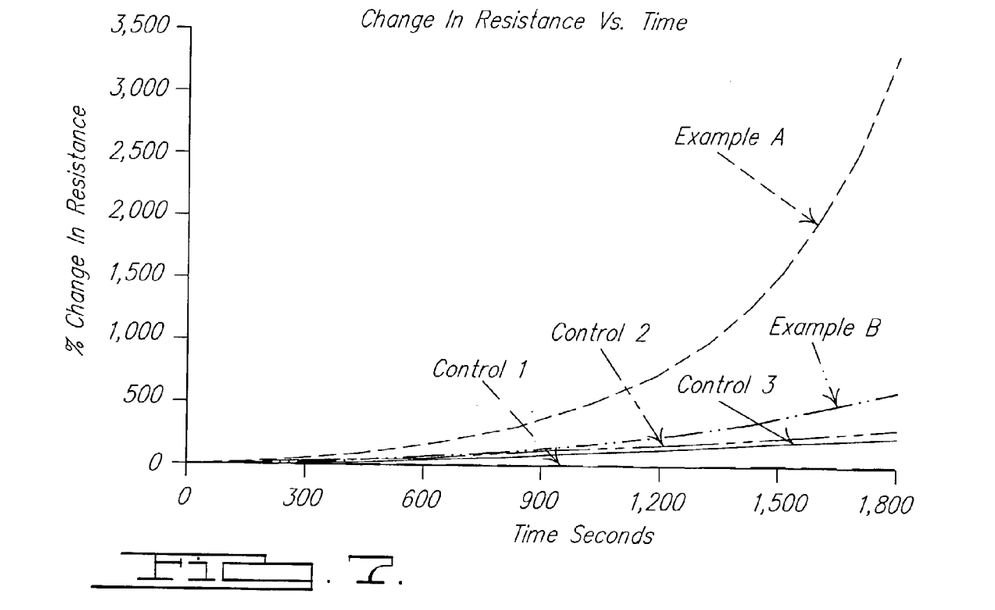
FIG. 7 is a chart of resistance versus time comparing prior art conductive particle sensor matrices with a preferred embodiment of the present invention.

It has been demonstrated that use of conductive carbon black particles 62, according to the present invention, in chemiresistor sensor films 22, significantly enhances the sensitivity of the sensor film 22 to chemical analytes over the prior art use of conductive particles. In FIG. 7, experimental data charting the percentage change of resistance versus time displays sensor sensitivity to exposure to 50 ml of 2-methylbutane solvent in a 8.5 liter container where the probes are positioned 14.3 cm above the solvent. All of the controls and examples described herein are prepared with 3–5% vinylmethylsiloxane-35–75% octylmethylsiloxane-20–62% dimethylsiloxane terpolymer (available as VAT 4326 from Gelest). Control 1 is a prior art conductive carbon black particle used in chemiresistor sensors having an $N_2$ value of 1475 $m^2/g$ and a DBP value of 365 ml/100 g, and is commercially available as EC 300J from Azko Nobel company Chicago, Ill. Control 2 has also been previously used as a chemiresistor sensor conductive carbon black and has an $N_2$ value of 26 $m^2/g$ and a DBP value of 65 ml/100 g and is commercially available as the product Raven® 410 P from Columbian Chemicals of Marietta, Ga. Control 3 is a matrix with prior art conductive carbon black having an $N_2$ value of 43 $m^2/g$ and a DBP of 121 ml/100 g N550 available commercially from Cabot Corporation. Example A is a conductive particle in a sensor film in accordance with the present invention, having an $N_2$ value of 14 and a DBP value of 85 ml/100 g. The conductive carbon black particles in Example A are commercially available, for example, from Asahi Carbon Company, Ltd. in Niigata, Japan under the trade name Asahi 15HS. Example B also has large conductive particles in accordance with the present invention having an $N_2$ value of 10 $m^2/g$ and a DBP of 30 ml/100 g which are commercially available as N880 from Cancarb, Ltd. located in Alberta, Canada. As shown in FIG. 7, the carbon black in Examples A and B demonstrate increased resistance for shorter time durations when compared with Control 1, 2, and 3. The more rapid change in resistance of Examples A and B indicates increased sensitivity to the presence of analytes in the surrounding environment. Further, Table 3 below also includes data showing the time to

|  | Control 1 | Control 2 | Control 3 | Example A | Example B |
|---|---|---|---|---|---|
| Siloxane VAT 4326 (%) | 96.9 | 96.9 | 96.9 | 96.9 | 96.9 |
| Carbon Black (phr) | 5 | 55 | 35 | 175 | 50 |
| Resistance at 25° C. (kOhms) | 18.0 | 23.9 | 20.3 | 26.9 | 28.0 |
| Resistance at 65° C. (kOhms) | 17.8 | 31.9 | 28.1 | 48.0 | 73.7 |
| 2× Resistance at 65° C. (kOhms) | 35.5 | 63.7 | 56.2 | 95.9 | 147.3 |
| Time to reach 2× resistance at 65° C. (seconds) | >1800 | 1320 | 1335 | 1215 | 975 | reach resistance at 65° C. and the value of 2 times resistance at 65° C., and time taken to reach the corresponding value, demonstrating improved response time for Examples A and B.

TABLE 2

One alternate preferred embodiment of the present invention incorporates all of the preferred embodiments described above into a sensor film 22 composition. The sensor film 22 has a crosslinked siloxane copolymer having at least one monomer with a large hydrocarbon side group. The present embodiment may also optionally include an alkyl substituted siloxane oil added to the siloxane base polymer 60 having at least one large hydrocarbon side group to further enhance sensor performance. Conductive particles 62 are also added, which are preferably large particle size carbon black conductive particles with an $N_2$ adsorption value of less than 25 and DBP absorption of less than about 180 ml/100 g. Testing of such sensor films 22 according to the present invention has demonstrated both increased temperature stability and analyte sensitivity when compared with known chemiresistor sensor films.

A preferred method of making the present invention includes forming the large hydrocarbon side group siloxane polymer by reacting a siloxane monomer having a functionalized hydrocarbon group with other siloxane monomers to polymerize the monomers together to form a copolymer. As previously discussed, preferably the resulting polymer structure is designed to have additional functional groups that facilitate subsequent crosslinking by a conventional hydrosilyation reaction, as recognized by one of skill in the art.

The siloxane polymer with a large hydrocarbon side group is further crosslinked. As previously discussed, this is preferably achieved through a hydrosilyation reaction by adding an appropriate curing reagent and a catalyst. The rate of reaction for crosslinking is dependent on temperature and is accelerated when temperature is raised; a catalyst is added; or both. Temperature may be used to control the rate of reaction to coincide with processing needs. Further, the addition of the catalyst may be prolonged until the mixture is ready to be processed for application onto the sensor. Preferably, the curing reagent is added in the range of about 1 to about 5 weight percent of the total polymer and curing reagent to form a polymer mixture. Preferably, catalyst is charged to the polymer mixture from about 0.05 to 1 weight percent of the total polymer mixture (excluding conductive particles).

A matrix mixture may be formed by admixing the conductive particles to the polymer mixture prior to charging with the catalyst. The plurality of conductive particles are added in a range of from about 25 to about 75% of the total mixture depending on particle characteristics, including tendency to disperse in the matrix. It is preferred that the conductive particles are well mixed into the polymer mixture for even distribution. The polymer or matrix mixture can be blended or mixed by equipment known in the art, such as for example, a mixer (e.g. a Banbury® or Brabender® mixer), a kneader, a monoaxial or biaxial extruder (e.g. single-screw or twin-screw extruders).

The handling and flowability of a matrix mixture is dependent on the rate of crosslinking once the catalyst is added, which effects the viscosity of the mixture. The amount of time that remains for handling is generally known as the "pot life", and may range from many hours at room temperature to less than an hour if temperatures are raised to above room temperature. The crosslinking or curing reaction may be prolonged by addition of inhibitors, which are well known in the art, as a means for retarding the reaction. The crosslinking or curing reaction can be performed entirely at room temperature, or may be accelerated by heating the mixture, depending on the processing needs. Such curing temperatures range from about 30° C. to about 250° C. The mixture is then applied to the sensor surface by conventional application means (e.g. doctor blade, casting, lamination, extrusion, pad printing, or silk screening). After application, further sensor components and processing may be completed, such as applying a protective cap. It is preferred that the curing occurs by placing the sensor with a matrix mixture applied into an oven at elevated temperature, for example, for 3 hours at 120° C. However, many variations of curing the siloxane polymer in the matrix mixture are feasible with the present invention.

Siloxane oil may be added to the polymer base either prior to placement on the sensor film (by mixing it into the matrix or polymer mixture) or after the sensor film is formed (e.g. if the sensor film is laminated or extruded, a vacuum assisted infusion of siloxane oil may be performed). The siloxane oil lacks functional groups which makes it inert to any crosslinking by hydrosilyation reaction, thus, for certain methods of crosslinking it can be added with the catalyst and curing reagent, without any chemical reaction with the siloxane polymer base. It is preferred that the siloxane oil is processed in such a manner that it does not crosslink.

EXAMPLE 1

A sensor film having a dimethylsiloxane polymer matrix with conductive carbon black and alkyl substituted siloxane oil is prepared by admixing the following materials: 85 parts by weight SP2224A (a first dimethylsilicone polymer having vinyl polymer and platinum available as a two-part system from SSP); 15 parts by weight (15 phr) polyOctylMethylsilicone oil; and 75 parts by weight N762 (a prior art carbon black available from Cabot Corporation having an $N_2$ value of 28 $m^2/g$ and a DBP of 65 ml/g), where the ingredients were mixed for 15 minutes in a Brabender® mixer to form a first mixture. A second mixture is formed by adding to a Brabender® mixture: 85 parts by weight SP2224B (a second dimethylsilicone polymer having hydride polymer as the second part of a two-part system from SSP); 15 parts by weight (15 phr) polyOctylMethylsilicone oil; and 75 parts by weight N762, where the ingredients are mixed for 15 minutes in a Brabender® mixer to form a second mixture. The first and second mixtures are combined and hand mixed for 5 minutes to form a matrix mixture, and then applied in a groove over electrodes in a sensor structure by a doctor blade. The sensor structure having the matrix mixture applied is then cured for 3 hours at 120° C.

EXAMPLE 2

A sensor film having a cross-linked large hydrocarbon side group substituted siloxane polymer matrix with large particle size conductive carbon black is prepared by adding the following materials into a mixer: 96.9 parts by weight VAT-4326 a (3–5% vinylmethylsiloxane)-(35–40% octylmethylsiloxane)-(dimethylsiloxane) terpolymer available from Gelest; 3.1 parts by weight HES 992 (a polyethylhydrosiloxane curing agent from Gelest); 0.1 parts by weight SIP 6829 (a platinum carbonyl cyclovinylmethylsiloxane catalyst complex); and 50 phr (parts per hundred resin) of Asahi 15HS (a large particle size carbon black available from Asahi Carbon Company having an $N_2$ value of 14 $m^2/g$ and a DBP of 85 ml/g). The materials are mixed in a Brabender® mixer for 15 minutes at 30° C. and 80 rpm to form a matrix mixture. The mixture is then applied in a groove over electrodes in a sensor structure by a doctor blade. The sensor structure having the matrix mixture applied is then cured for 3 hours at 120° C.

EXAMPLE 3

A sensor film having a cross-linked large hydrocarbon side group substituted siloxane polymer matrix with large particle size conductive carbon black is prepared by adding the following materials into a mixer: 96.9 parts by weight VAT-4326 a (3–5% vinylmethylsiloxane)-(35–40% octylmethylsiloxane)-(dimethylsiloxane) terpolymer available from Gelest; 3.1 parts by weight HES 992 (a polyethylhydrosiloxane curing agent from Gelest); 0.1 parts by weight SIP 6829 (a platinum carbonyl cyclovinylmethylsiloxane catalyst complex); and 175 phr (parts per hundred resin) of N880 (a large particle size carbon black available from Cancarb Ltd. having an $N_2$ value of 10 $m^2/g$ and a DBP of 30 ml/g). The materials are mixed in a Brabender® mixer for 15 minutes at 30° C. and 80 rpm to form a matrix mixture. The mixture is then applied in a groove over electrodes in a sensor structure by a doctor blade. The sensor structure having the matrix mixture applied is then cured for 3 hours at 120° C.

EXAMPLE 4

The preparation of crosslinked hydrocarbon side group substituted siloxane copolymer with large particle size conductive carbon black is conducted as follows. The following materials are weighed into a 30 ml Brabender® mixer and mixed for 15 minutes at 80 rpm at a mix temperature of 30° C.: 96.9 parts by weight VAT-4326 (a Vinylmethylsiloxane-octylmethylsiloxane-dimethylsiloxane terpolymer available from Gelest); 3.1 parts by weight HES-992 (a polyethylhydrosiloxane curing agent available from Gelest); 0.1 parts by weight SIP 6829 (a platinum catalyst available from Gelest); and 75 parts by weight Raven 410P (non-reinforcing large particle size carbon black available from Columbian Chemicals of Marietta, Ga.). The matrix mixture is then applied in a groove over the electrodes in a sensor structure by a doctor blade. The sensor film is cured in an oven for 3 hours at 120° C.

EXAMPLE 5

The preparation of crosslinked hydrocarbon side group substituted siloxane homopolymer with large particle size conductive carbon black is prepared by admixing the following materials into a 72 ml FlackTec® DAC 150FVZ-K model mixer and mixed for approximately 6 minutes at 2750 rpm at a mix temperature of 30° C.: 95.18 parts by weight (phr) of PMV-9925 (a vinyl terminated polyphenylmethylsiloxane available from Gelest); 4.82 parts by weight HES-992 (a polyethylhydrosiloxane curing agent available from Gelest); 0.1 parts by weight SIP 6826 (a platinum catalyst available from Gelest); and 30 parts by weight Asahi HS 15 Asahi 15 HS (a large particle size carbon black available from Asahi Carbon Company having an $N_2$ value of 14 $m^2/g$ and a DBP of 85 ml/g). The matrix mixture is then applied in a groove over the electrodes in a sensor structure by a doctor blade. The sensor film is cured in an oven for 3 hours at 120° C.

The sensor films according to the present invention provide improved sensor stability during temperature fluctuations, thus enhancing the accuracy of the sensor readings of analyte concentration by making it less dependent on variations in temperature. Further, the present invention provides increased sensitivity to target analytes over the prior art sensor films, improving the sensor film operation. The description of the invention and examples provided herein is merely exemplary in nature and, thus, variations that do not depart from the gist of the invention are intended to be within the scope of the invention. Such variations are not to be regarded as a departure from the spirit and scope of the invention.

What is claimed is:

1. A conductometric sensor film comprising:
   a crosslinked siloxane polymer comprising a monomer having an alkyl hydrocarbon side group with greater than or equal to two carbon atoms; and
   a plurality of conductive carbon black particles having a $N_2$ adsorption of between about 8 to about 25 $m^2/g$, distributed within said polymer, wherein the film exhibits a change in resistance when monomer interacts with one or more target analytes comprising one or more volatile organic hydrocarbon compounds.

2. The conductometric sensor film according to claim 1, further comprising an alkyl side group substituted siloxane oil, wherein said alkyl side group has greater than or equal to two carbon atoms.

3. The conductometric sensor film according to claim 1, wherein said polymer further comprises a second hydrocarbon side group selected from the group consisting of: alkyl, aryl, alkenes, and aromatics.

4. The conductometric sensor film according to claim 1, wherein said hydrocarbon side group comprises a hydrocarbon comprising a polar group.

5. The conductometric sensor film according to claim 1, wherein said conductive carbon black particles have a DBP value of from about 1 to about 180 ml/100 g.

6. The conductometric sensor film according to claim 1, wherein said crosslinked polymer comprises poly(vinylmethylsiloxane octylmethylsiloxane-dimethylsiloxane).

7. The conductometric sensor film according to claim 1, wherein said crosslinked siloxane polymer further comprises polyphenylmethylsiloxane.

8. A sensor film composition for detecting chemical analytes comprising:
   a crosslinked polymer comprising a siloxane monomer having an alkyl hydrocarbon side group with greater than or equal to two carbon atoms; and
   a plurality of conductive particles distributed in said crosslinked polymer, wherein the film exhibits a change in resistance when said monomer interacts with one or more target analytes comprising one or more volatile organic hydrocarbon compounds.

9. The sensor film composition according to claim 8, wherein said polymer further comprises a second hydrocarbon side group selected from the group consisting of: alkyl, aryl, alkenes, and aromatics.

10. The sensor film composition according to claim 8, wherein said hydrocarbon side group comprises a hydrocarbon comprising a polar group.

11. The sensor film composition according to claim 8, wherein said hydrocarbon side group is selected from the group consisting of: ethyl, propyl, butyl, pentyl, hexyl, heptyl, octyl, nonyl, decyl, alkylphenyl, and phenylpropyl.

12. The sensor film composition according to claim 8, wherein said polymer further comprises a second hydrocarbon side group selected from the group consisting of: butylated aryloxypropyl, N-pyrrolidonepropyl, cyanopropyl, benzyltrimethyl ammonium chloride, and hydroxyalkyl.

13. The sensor film composition according to claim 8, wherein said crosslinked polymer comprises poly(vinylmethylsiloxane-octylmethylsiloxane-dimethylsiloxane).

14. The sensor film composition according to claim 8, wherein said crosslinked polymer further comprises polyphenylmethylsiloxane.

15. The sensor film composition according to claim 8, wherein said conductive particles are selected from the group consisting of: gold, platinum, graphite, carbon black, nickel, conductive metal borides, nitrides and carbides, nickel, and mixtures thereof.

16. The sensor film composition according to claim 8, wherein said plurality of conductive carbon black particles have an $N_2$ adsorption of between about 8 to 25 $m^2/g$, distributed within said cross linked polymer.

17. The sensor film composition according to claim 8, wherein said plurality of conductive carbon black particles have an $N_2$ adsorption of between about 8 to about 25 $m^2/g$ and a DBP value of from about 1 to about 180 ml/100 g.

18. A conductometric sensor film according to claim 1, wherein said change in resistance is detectable by a sensing apparatus in electrical communication with said film.

19. A conductometric sensor film according to claim 1, wherein said alkyl hydrocarbon side has greater than or equal to six carbon atoms.

20. A conductometric sensor film according to claim 8, wherein said change in resistance is detectable by a sensing apparatus in electrical communication with said film.

21. A conductometric sensor film according to claim 8, wherein said alkyl hydrocarbon side has greater than or equal to six carbon atoms.

22. A conductometric sensor probe comprising:
a film; and
at least one electrode in electrical communication with said film; wherein said film comprises a crosslinked siloxane polymer comprising a monomer having an alkyl hydrocarbon side group with greater than or equal to two carbon atoms and a plurality of conductive particles distributed in said polymer to form a matrix, wherein said conductive particles have an $N_2$ adsorption of between 8 to about 25 $m^2/g$; wherein said film exhibits a detectable change in resistance in the presence of one or more target analytes comprising one or more volatile organic hydrocarbon compounds.

* * * * *